United States Patent [19]

Yamazaki et al.

[11] Patent Number: 5,342,983
[45] Date of Patent: Aug. 30, 1994

[54] ORGANIC SILICON COMPOUNDS

[75] Inventors: Toshio Yamazaki; Hideki Sugahara; Shoji Ichinohe, all of Annaka; Toshinobu Ishihara; Tohru Kubota, both of Joetsu, all of Japan

[73] Assignee: Shin-Etsu Chemical Co., Ltd., Tokyo, Japan

[21] Appl. No.: 26,792

[22] Filed: Mar. 5, 1993

[30] Foreign Application Priority Data

Mar. 5, 1992 [JP] Japan ................... 4-083438

[51] Int. Cl.$^5$ ................ C07F 7/08; C07F 7/10; C07F 7/18
[52] U.S. Cl. ................... 556/445; 556/413; 556/425; 556/415; 556/429
[58] Field of Search ............... 556/445, 415, 425, 429, 556/413

[56] References Cited

U.S. PATENT DOCUMENTS 5,210,252  5/1993  Kubota et al. ............... 556/445

*Primary Examiner*—Paul F. Shaver
*Attorney, Agent, or Firm*—Millen, White, Zelano & Branigan

[57] ABSTRACT

Organic silicon compounds which are expressed by the general chemical formulae (I) or (II):

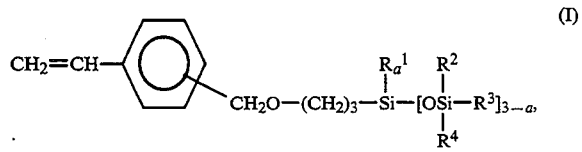

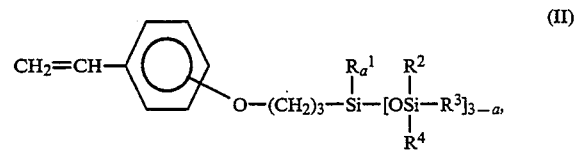

wherein $R^1$ is a monovalent organic group with 1 to 8 carbon atoms; $R^2$, $R^3$ and $R^4$ in each equation are independent and either a monovalent organic group with 1 to 8 carbon atoms or a siloxyl group expressed by

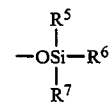

wherein $R^5$, $R^6$ and $R^7$ are independent in each equation and they are a monovalent organic group with 1 to 8 carbon atoms; and a is either 0, 1 or 2. The novel organic silicon compounds possess both a polymerizable double bond and organopolysiloxane within the same molecule. These compounds are superior in their polymerizability and copolymerizability and are useful as polymer reforming agents.

10 Claims, 4 Drawing Sheets

ORGANIC SILICON COMPOUNDS

BACKGROUND OF THE INVENTION

This invention relates to novel organic silicon compounds. These compounds are useful as, for example, a reforming agent in order to convert various polymer materials into siloxanes.

Currently, known organic silicon compounds which possess both a polymerizable double bond and organopolysiloxane within the same molecule are of the methacrylic type and the styrene type, such as $$CH_2=\underset{\underset{O}{\|}}{\overset{\overset{CH_3}{|}}{C}}-C-O-(CH_2)_3-Si-[OSi-(CH_3)_3]_3,$$

and $$CH_2=CH-\phenyl-Si-[OSi-(CH_3)_3]_3$$

These compounds are utilized as reforming agents for converting polymer materials into siloxanes by the methods of copolymerization and grafting.

SUMMARY OF THE INVENTION

This invention relates to organic silicon compounds which possess both a polymerizable double bond and organopolysiloxane within the same molecule. Organic silicon compounds of this invention are novel compounds, which possess a highly polymerizable double bond as well as organopolysiloxane within the same molecule.

These organic silicon compounds are of the general chemical formula (I):

$$CH_2=CH-\phenyl-CH_2O-(CH_2)_3-\underset{\underset{R^4}{|}}{\overset{\overset{R_a^1}{|}}{Si}}-[O\underset{\underset{}{}}{\overset{\overset{R^2}{|}}{Si}}-R^3]_{3-a}, \quad (I)$$

wherein

R$^1$ is a monovalent organic group with 1 to 8 carbon atoms;

R$^2$, R$^3$ and R$^4$ are independently either a monovalent organic group with 1 to 8 carbon atoms or a siloxyl group of the formula $$-O\underset{\underset{R^7}{|}}{\overset{\overset{R^5}{|}}{Si}}-R^6$$

wherein R$^5$, R$^6$ and R$^7$ are the same or different and are a monovalent organic group with 1 to 8 carbon atoms; and is either 0, 1 or 2, or of the general chemical formual (II):

$$CH_2=CH-\phenyl-O-(CH_2)_3-\underset{\underset{R^4}{|}}{\overset{\overset{R_a^1}{|}}{Si}}-[O\underset{\underset{}{}}{\overset{\overset{R^2}{|}}{Si}}-R^3]_{3-a}, \quad (II)$$

wherein

R$^1$ is a monovalent organic group with 1 to 8 carbon atoms;

R$^2$, R$^3$ and R$^4$ are independently either a monovalent organic group with 1 to 8 carbon atoms or a siloxyl group of the formula $$-O\underset{\underset{R^7}{|}}{\overset{\overset{R^5}{|}}{Si}}-R^6$$

wherein R$^5$, R$^6$ and R$^7$ are the same or different and are a monovalent organic group with 1 to 8 carbon atoms; and a is either 0, 1 or 2.

In the above general formulae (I) and (II), examples of R$^1$, R$^2$, R$^3$, R$^4$, R$^5$, R$^6$ and R$^7$, which are a monovalent organic group with 1 to 8 carbon atoms, are C$_{1-8}$-hydrocarbon groups, optionally substituted with halogen, cyano, amino, nitro, glyceryl and/or mercapto groups. For example: alkyl groups such as a methyl group, ethyl group, propyl group, and a butyl group; cycloalkyl groups such as a cyclopentyl group and a cyclohexyl group; aryl groups such as a phenyl group; aralkyl groups such as a benzyl group; alkenyl groups such as a vinyl group and an allyl group; and substituted hydrocarbon groups such as chloromethyl, 4-chlorophenyl, 4-chlorobenzyl, 2-cyanoethyl, 3-aminopropyl, 4-aminopropyl, 4-nitrophenyl, 3-glycerylpropyl, 3-mercaptopropyl and 3,3,3-trifluoropropyl groups. Examples of siloxyl groups which are expressed by $$-O\underset{\underset{R^7}{|}}{\overset{\overset{R^5}{|}}{Si}}-R^6$$

are: a trimethyl siloxyl group, ethyl dimethyl siloxyl group, phenyl dimethyl siloxyl group, vinyl dimethyl siloxyl group, chloromethyl dimethyl siloxyl group and a 3,3,3-trifluoropropyl dimethyl siloxyl group. Each R$^1$, R$^2$, R$^3$, R$^4$, R$^5$, R$^6$ and R$^7$ in one molecule may be the same or different. A preferred compound is that wherein each R group is a methyl group when the compound is utilized as a polymer reforming agent.

Organic silicon compounds of this invention, which are expressed by the said general formulae (i) and (II), are synthesized, for example, by the methods indicated below:

$$CH_2=CH-\phenyl-CH_2O-CH_2CH=CH_2 \quad + \quad (1)$$

-continued

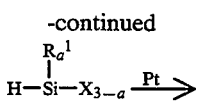

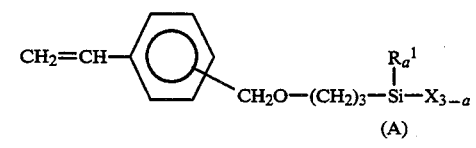

(A)

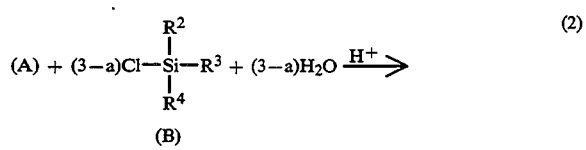

(B)

(2)

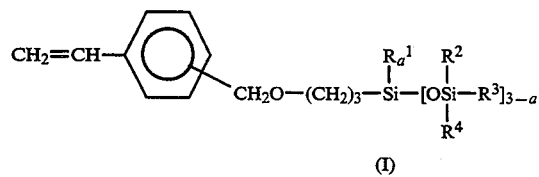

(I)

$(3-a)HCl + (3-a)HX$

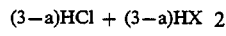

(3)

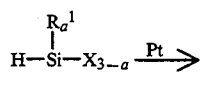

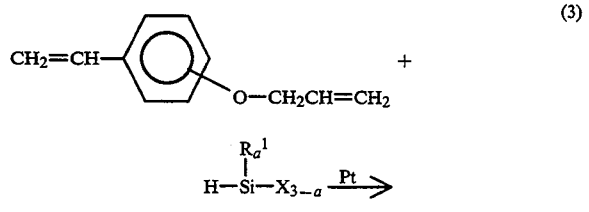

(C)

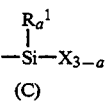

(B)

(4)

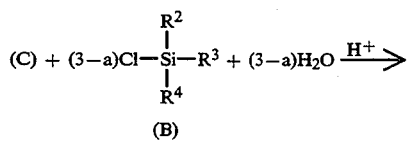

(II)

$(3-a)HCl + (3-a)HX$ wherein X designates either halogen atoms such as chlorine and bromine, groups which are readily hydrolyzed such as alkoxyl groups with 1 to 4 carbon atoms, or a hydroxyl group, and $R^1$ through $R^4$ and a are the same as described above.

Among the compounds listed above, a synthesis of the intermediate compound (A) in the equation (1) can be performed by following the method described in Japanese patent application 3-350090. Examples of the compound (A) suitable to this invention are: 3-(4-vinyl-benzyloxy)-propyltrichlorosilane, 3-(4-vinylbenzyloxy) propylmethyl-dichlorosilane, 3-(4-vinylbenzyloxy) propyldimethyl-chlorosilane, 3-(3-vinylbenzyloxy)propyltrichlorosilane, 3-(3-vinylbenzyloxy)propyl-methyldichlorosilane, 3-(3-vinylbenzyloxy) propyl-dimethylchlorosilane, 3-(4-vinylbenzyloxy) propyl-trimethoxysilane, 3-(4-vinylbenzyloxy)propyl-methyl-dimethoxysilane, 3-(4-vinylbenzyloxy)propyl-dimethyl-methoxysilane, 3-(3-vinylbenzyloxy)propyl-trimethoxysilane, 3-(3-vinylbenzyloxy) propyl-methyl-dimethoxysilane, 3-(3-vinylbenzyloxy)propyl-dimethyl-methoxysilane, 3-(4-vinylbenzyloxy)propyl-triethoxysilane, 3-(4-vinylbenzyloxy) propyl-methyl-diethoxysilane, 3-(4-vinylbenzyloxy)propyl-dimethyl-ethoxysilane, 3-(3-vinylbenzyloxy)propyl-triethoxysilane, 3-(3-vinylbenzyloxy)propylmethyl-dimethoxysilane, and 3-(3-vinylbenzyloxy)propyldimethyl-ethoxysilane.

The synthesis of the organic silicon compound (I) through the equation (2) can be carried out by adding the mixed solution of the said compound (A) and chlorosilane (B) drop by drop into a solvent mixture such as water/methanol/toluene, followed by separation of the water layer after maturity of the reaction, then the washing, condensation, and purification of the organic layer. This general method is known and the selection of a reaction temperature, reaction time, solvent, catalyst, and purification method follow the known conditions. However, the intended product, the organic silicon compound (I) possesses the highly reactive styrene type double bond, which requires some cautions. Therefore, the generally known polymerization inhibitors are utilized as necessary which is a desirable procedure and will not inhibit the reaction. These polymerization inhibitors are, for example, hydroquinone, 4-methoxyphenol, 2,6-di-tert-butyl-4-cresol, 2,2'-methylenebis(4-ethyl-6-tert-butylphenol), and para-tert-butyl-catechol.

Examples of chlorosilane (B) are: trimethylchlorosilane, ethyl-dimethyl-chlorosilane, phenyl-dimethyl-chlorosilane, vinyl-dimethyl-chlorosilane, chloromethyldimethyl-chlorosilane, 3,3,3-trifluoropropyl-dimethylchlorosilane, chloropentamethyl-disiloxane, 1-chloroheptamethyl-trisitoxane, 3-chloroheptamethyl-trisiloxane, and 3-chloro-3-trimethyl-siloxy-hexamethyl-trisiloxane. Among these, trimethyl-chlorosilane is the most desirable.

Further, the utilization of silanol compounds expressed by

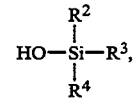

instead of the chlorosilane (B) in the equation (2), also leads to the intended compound (I), through the elimination reactions of the hydrogen halide and the alcohol when X is a halogen and an alkoxyl group, respectively.

The synthesis of the compound (C) by following the equation (3) can be carried out by the method described in Japanese patent application 3-213503. Examples of the compound (C) suitable for this invention are: 3-(4-vinylphenoxy) propyl-trichlorosilane, 3-(4-vinylphenoxy)propylmethyl-dichlorosilane, 3-(4-vinylphenoxy) propyl-dimethylchlorosilane, 3-(3-vinylphenoxy)propyl-trichlorosilane, 3-(3-vinylphenoxy)-propyl-methyl-dichlorosilane, 3-(3-vinylphenoxy)propyl-dimethyl-chlorosilane, 3-(4-vinylphenoxy)propyl-trimethoxysilane, 3-(4-vinylphenoxy) propyl-methyl-dimethoxysilane, 3-(4-vinylphenoxy)propyl-dimethyl-methoxysilane, 3-(3-vinylphenoxy)propyl-trimethoxysilane, 3-(3-vinylphenoxy)propyl-methyl-dimethoxysilane, 3-(3-vinylphenoxy)propyl-dimethyl-methoxysilane, 3-(4-vinylphenoxy)propyl-triethoxysilane, 3-(4-vinylphenoxy)propyl-methyl-diethoxysilane, 3-(4-vinylphenoxy)propyl-dimethyl-ethoxysilane, 3-(3-vinylphenoxy) propyl-triethoxysilane, 3-(3-vinylphenoxy)propyl-methyl-diethoxysilane, and 3-(3-vinylphenoxy)propyl-dimethyl-ethoxysilane.

The synthesis of the organic silicon compound (II) through the reaction in the equation (4) is carried out by the similar method as the synthesis of the organic silicon compound (I), using the compound (C) in place of the compound (A). Use of the polymerization inhibitors is, of course, similar to the case of the organic silicon compound (I). Further, the utilization of silanol compounds expressed by

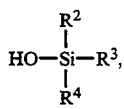

instead of the chlorosilane (B), similarly leads to the intended compound (II), as seen in the case of the organic silicon compound (I).

This invention offers novel organic silicon compounds with both a polymerizable double bond and organopolysitoxane within the same molecule. Compounds of this invention are superior in their polymerizability and copolymerizability and provide special characteristics, such as heat resistance, weather resistance, surface characteristics, and gas permeability, to polymer materials. Therefore, these compounds are useful as polymer reforming agents.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding Japanese application 4-83438, filed Mar. 5, 1992, are hereby incorporated by reference.

EXAMPLES

Example 1

A silane mixed solution (a) was prepared by mixing 29.6 g (0.1 mol) of 3-(4-vinylbenzyloxy)propyl-trimethoxysilane and 130.2 g (1.2 mol) of trimethyl-chlorosilane. 200 ml of water, 100 ml of methanol, 100 ml of toluene, and 17 g of a concentrated hydrochloric acid as a catalyst were placed into a flask equipped with a dropping funnel, a condenser, a thermometer, and a stirring instrument. This mixture was stirred while cooled and the silane mixed solution (a) was added drop by drop at the temperature of at most 20° C. After about two hours of reaction maturing at room temperature, it was separated and the organic layer was washed with a saturated sodium chloride solution until it became neutral. It was then desiccated with anhydrous sodium sulfate and the solvent was distilled off under reduced pressure. 0.5 wt.% of 2,2'-methylenebis(4-ethyl-6-tert-butylphenol) was added to the above crude distillation solution as a polymerization inhibitor and it was further purified by distillation through the rectifying tower. The obtained amount of the product was 26.3 g (a yield of 56%) and the product was identified by the methods of IR, $^1$H-NMR, MS, and elemental analysis to be the intended product expressed by the following equation:

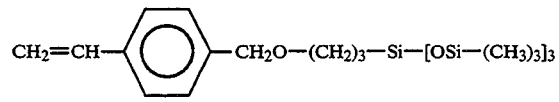

The analytical results are shown as follows:

IR (Cm$^{-1}$):
3090 (CH$_2$=CH), 2960 (C-H), 1250 (Si-CH$_3$), 1190 (Si-O),
1060 (Si-O), 840 (1,4-substituted benzene)

$^1$H-NMR δ(ppm), solvent: CCl$_4$: 0.13 (s, 27H, Si-—CH$_3$), 0.3 to 0.7 (m, 2H, C—CH$_2$—Si), 1.3 to 1.9 (m, 2H, C—CH$_2$—C), 3.3 (t, 2H, O—CH$_2$—C), 4.4 (s, 2H, Φ—CH$_2$—O), 4.9 to 6.8 (m, 3H, CH$_2$=CH—Φ), 7.2 (s, 4H, 1,4-substituted benzene)

MS M+ (m/e): 470

Figure 1:
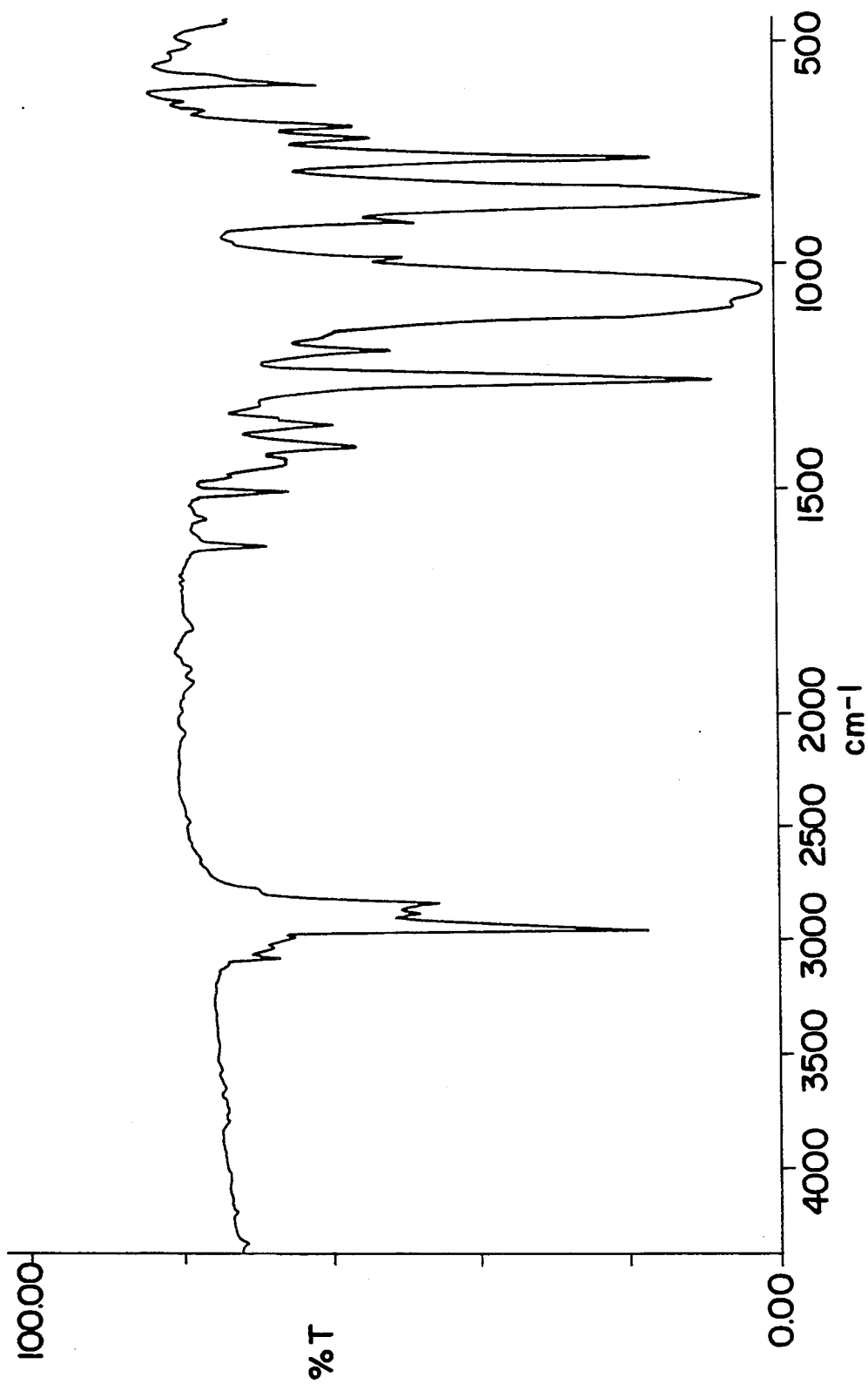
FIG. 1 presents the IR spectrum of the intended compound which was obtained in Example 1.
Figure 2:
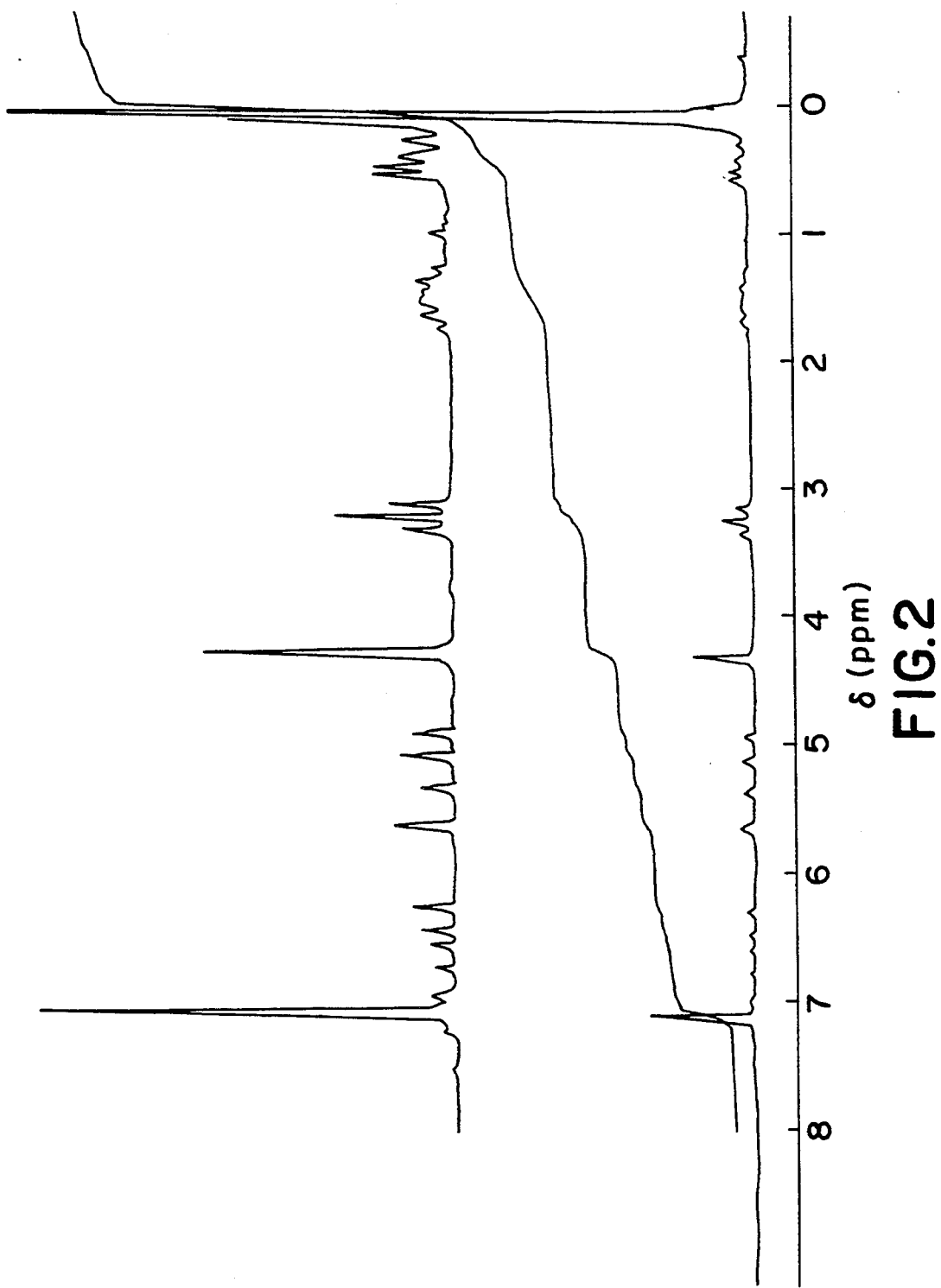
FIG. 2 presents the $^1$H-NMR spectrum of the intended compound which was obtained in Example 1.

Elemental Analysis %: values in parentheses are theoretical values:

C 53.73 (53.62), H 8.90 (8.94), Si 23.94 (23.83):

IR and $^1$H-NMR spectra are shown in FIGS. 1 and 2, respectively.

EXAMPLE 2

A purified product was obtained by the similar method as described in Example 1, except that a mixed solution (b) which comprises 26.9 g (0.1 mol) of 3-(4-vinylbenzyloxy) propyl-dimethyl-chlorosilane and 43.4 g (0.4 mol) of trimethyl-chlorosilane was employed instead of the silane mixed solution (a) and that no hydrochloric acid catalyst was used. The obtained amount of product was 15.1 g (a yield of 47%) and it was identified by the methods of IR, $^1$H-NMR, MS, and elemental analysis to be the intended product expressed by the following equation:

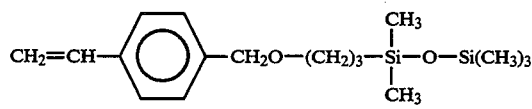

The analytical results are shown as follows:
IR (cm$^{-1}$):
3090 (CH$_2$=CH), 2960 (C—H), 1250 (Si—CH$_3$), 1190 (Si—O),
1060 (Si—O), 840 (1,4-substituted benzene)

$^1$H-NMR δ (ppm), solvent: CCl$_4$: 0.13 (s, 15H, Si—CH$_3$), 0.3 to 0.7 (m, 2H, C—CH$_2$—Si), 1.3 to 1.9 (m, 2H, C—CH$_2$—C), 3.3 (t, 2H, O—CH$_2$—C), 4.4 (s, 2H, Φ—CH$_2$—O), 4.9 to 6.8 (m, 3H, CH$_2$=CH—Φ), 7.2 (s, 4H, 1,4-substituted benzene)

MS M$^+$ (m/e: 322

Elemental Analysis %: values in parentheses are theoretical values:

C 63.51 (63.35), H 9.21 (9.32), Si 17.42 (17.39):

EXAMPLE 3

A silane mixed solution (c) was prepared by mixing 28.2 g (0.1 mol) of 3-(4-vinylphenoxy) propyl-trimethoxysilane and 130.2 g (1.2 mol) of trimethylchlorosilane. 200 ml of water, 100 ml of methanol, 100 ml of toluene, and 17 g of a concentrated hydrochloric acid as a catalyst were placed into a flask equipped with a dropping funnel, a condenser, a thermometer, and a stirring instrument. This mixture was stirred while cooled and the silane mixed solution (c) was added drop by drop at the temperature of at most 20° C. After two hours of reaction maturing at room temperature, it was separated and the organic layer was washed with a saturated sodium chloride solution until it became neutral. It was then desiccated with anhydrous sodium sulfate and the solvent was distilled off under reduced pressure. 0.5 wt.% of 2,2'-methylenebis(4-ethyl-6-tert-butylphenol) was added to the above crude distillation solution as a polymerization inhibitor and it was further purified by distillation through the rectifying tower. The obtained amount of the product was 19.2 g (a 42% yield) and the product was identified by the methods of IR, $^1$H-NMR, MS, and elemental analysis to be the intended product expressed by the following equation:

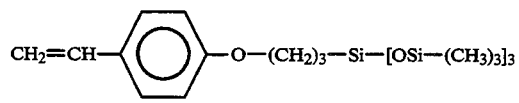

The analytical results are shown as follows:
IR (cm$^{-1}$):
3090 (CH$_2$=CH), 2960 (C—H), 1250 (Si—CH$_3$), 1190 (Si—O),
1060 (Si—O), 840 (1,4-substituted benzene)

$^1$H-NMR δ(ppm), solvent: CCl$_4$: 0.13 (s, 27H, Si—CH$_3$), 0.4 to 0.8 (m, 2H, C—CH$_2$-Si), 1.5 to 2.0 (m, 2H, C—CH$_2$—C), 3.8 (t, 2H, O—CH—$_2$C), 4.8 to 6.8 (m, 3H, CH$_2$—CH—Φ), 6.6 to 7.3 (m, 4H, 1,4-substituted benzene)

Figure 3:
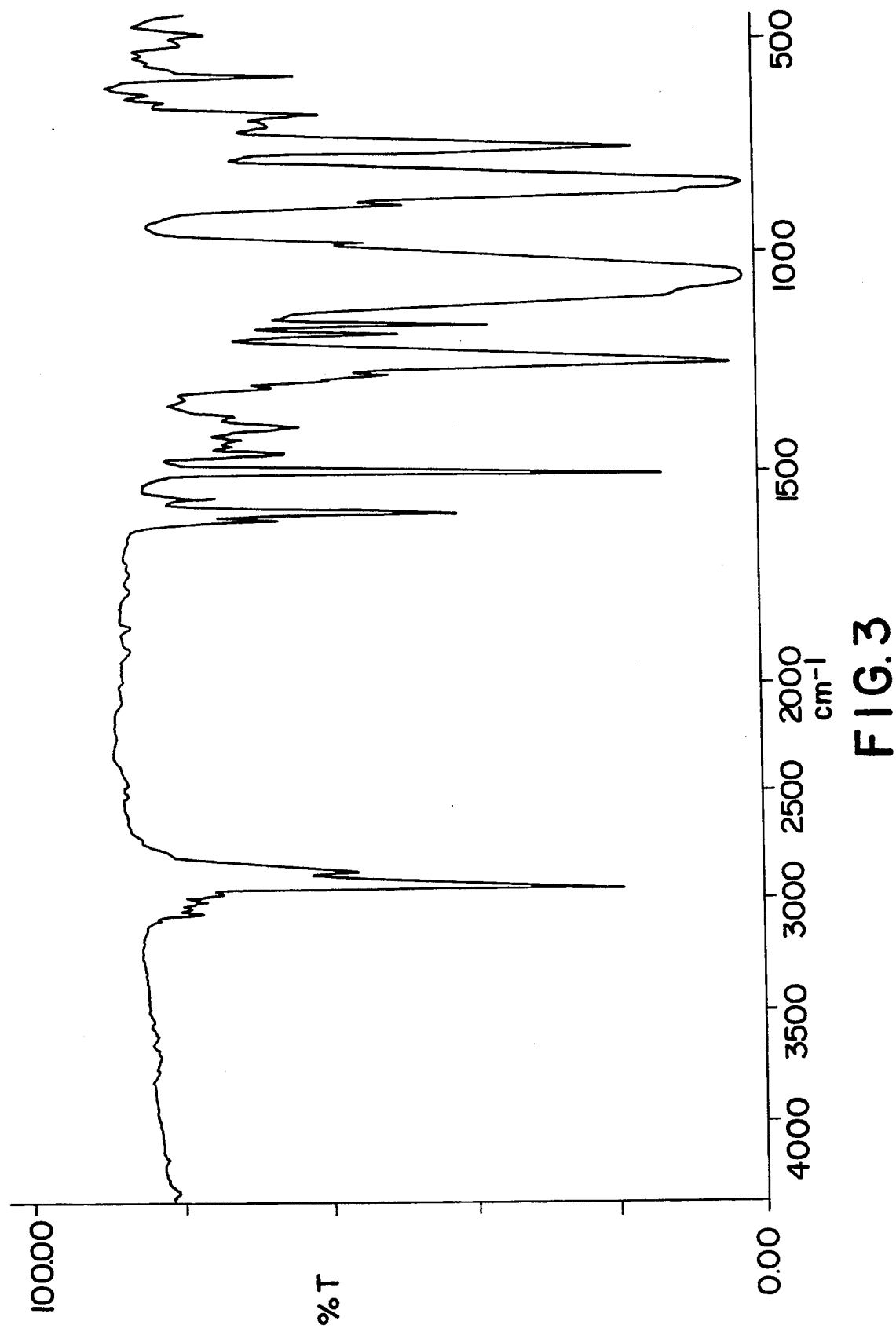
FIG. 3 presents the IR spectrum of the intended compound which was obtained in Example 3.
Figure 4:
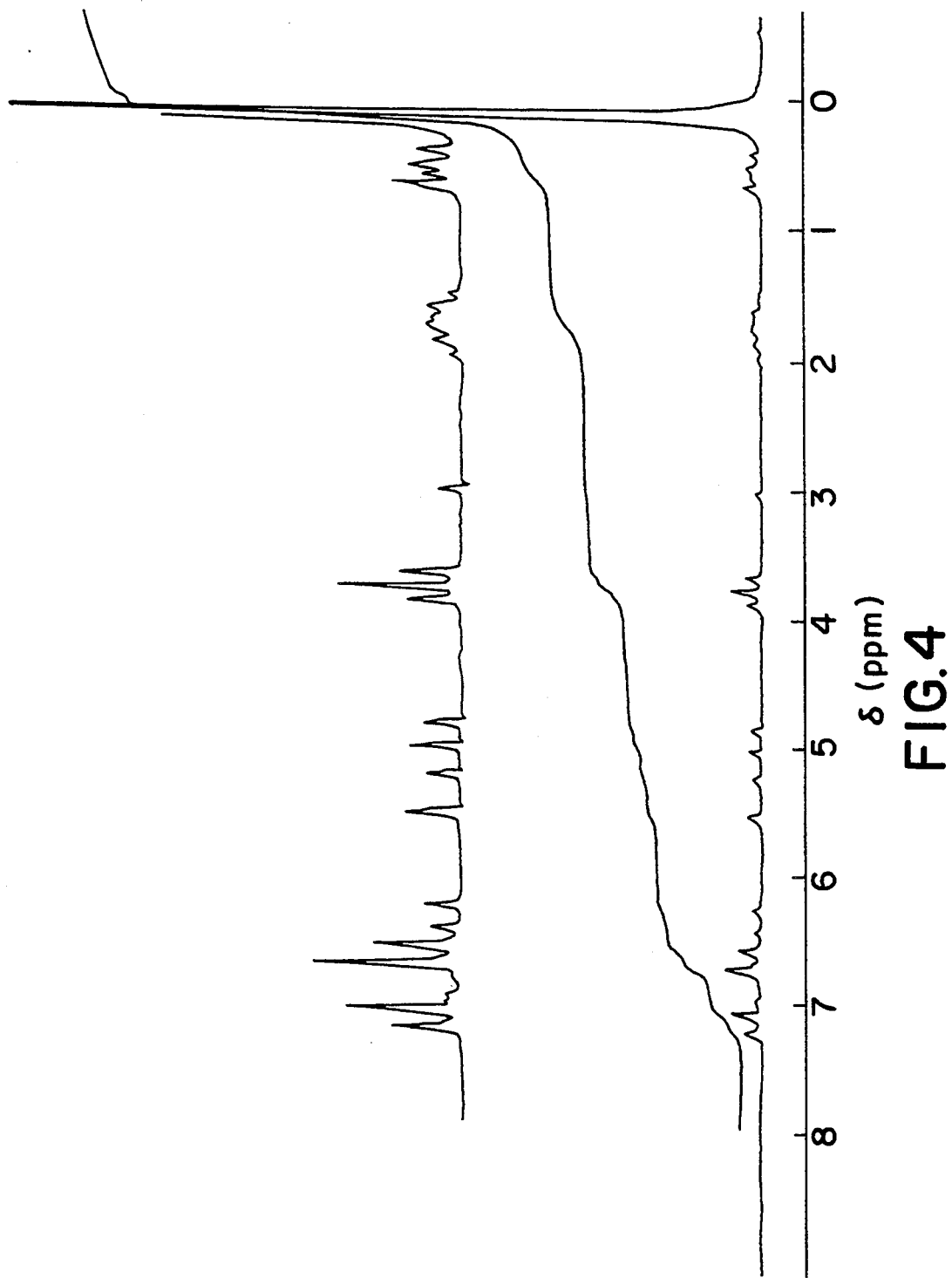
FIG. 4 presents the $^1$H-NMR spectrum of the intended compound which was obtained in Example 3.

MS M$^+$ (m/e)$_4$:

Elemental Analysis %: values in parentheses are theoretical values:

C 52.65 (52.63), H 8.59 (8.77), Si 24.67 (24.56):

IR and $^1$H-NMR spectra are shown in FIGS. 3 and 4, respectively.

EXAMPLE 4

A purified product was obtained by the similar method as described in Example 3, except that a mixed solution (d) which comprises 25.5 g (0.1 mol) of 3-(4-vinylphenoxy)propyl-dimethyl-chlorosilane and 43.4 g (0.4 mol) of trimethyl-chlorosilane was employed instead of the silane mixed solution (c) and that no hydrochloric acid catalyst was used. The obtained amount of product was 11.7 g (a yield of 38%) and it was identified by the methods of IR, $^1$H-NMR, MS, and elemental analysis to be the intended product expressed by the following equation:

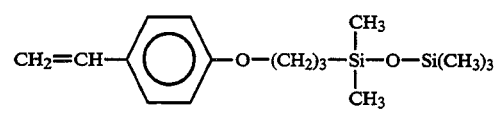

The analytical results are shown as follows:
IR (cm$^{-1}$):
3090 (CH$_2$=CH), 2960 (C—H), 1250 (Si—CH$_3$), 1190 (Si—O),
1060 (Si—O), 840 (1,4-substituted benzene)

$^1$H-NMR δ(ppm), solvent: CCl$_4$: 0.13 (s, 15H, Si—CH$_3$), 0.4 to 0.8 (m, 2H, C—CH$_2$—Si), 1.5 to 2.0 (m, 2H, C—CH$_2$—C), 3.8 (t, 2H, O—CH$_2$—C), 4.8 to 6.8 (m, 3H, CH$_2$=CH—Φ) 6.6 to 7.3 (m, 4H, 1,4-substituted benzene)

MS M$^+$ (m/e): 308

Elemental Analysis %: values in parentheses are theoretical values:

C 62.51 (62.34), H 8.97 (9.09), Si 18.32 (18.18):

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Organic silicon compounds of the chemical formula (I):

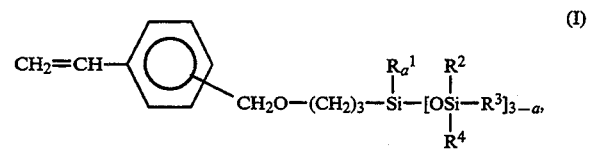

wherein

R$^1$ is a monovalent hydrocarbon group of 1 to 8 carbon atoms;

R$^2$, R$^3$ and R$^4$ are independently either a monovalent hydrocarbon group of 1 to 8 carbon atoms or a siloxyl group of the formula

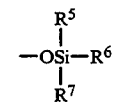

wherein $R^5$, $R^6$ and $R^7$ are independently a monovalent hydrocarbon group of 1 to 8 carbon atoms; and a is either 0, 1 or 2, the monovalent hydrocarbon groups of $R^1$, $R^2$, $R^3$, $R^4$, $R^5$, $R^6$ and $R^7$ being optionally substituted by halogen, cyano, amino, nitro, glyceryl or mercapto group(s).

2. Organic silicon compounds of the chemical formula (II):

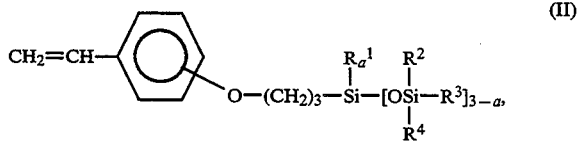

wherein $R^1$ is a monovalent hydrocarbon group of 1 to 8 carbon atoms;

$R^2$, $R^3$ and $R^4$ are independently either a monovalent hydrocarbon group of 1 to 8 carbon atoms or a siloxyl group of the formula

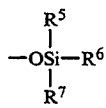

wherein $R^5$, $R^6$ and $R^7$ are independently a monovalent hydrocarbon group of 1 to 8 carbon atoms; and a is either 0, 1 or 2, the monovalent hydrocarbon groups of $R^1$, $R^2$, $R^3$, $R^4$, $R^5$, $R^6$ and $R^6$ being optionally substituted by halogen, cyano, amino, nitro, glyceryl or mercapto group(s).

3. The organic silicon compounds of claim 1, wherein $R^1$, $R^2$, $R^3$, and $R^4$ are each independently alkyl, cycloalkyl, phenyl, benzyl or alkenyl optionally substituted with halogen atom(s).

4. The organic silicon compounds of claim 1, wherein each of $R^1$, $R^2$, $R^3$ and $R^4$ is a methyl group.

5. The organic silicon compounds of claim 1, wherein each of $R^2$, $R^3$, and $R^4$ are a siloxyl group and each of $R^1$, $R^5$, $R^6$ and $R^7$ are independently alkyl, cycloalkyl, phenyl, benzyl or alkenyl optionally substituted with halogen atom(s).

6. The organic silicon compounds of claim 1, wherein each of $R^1$, $R^5$, $R^6$ and $R^7$ is a methyl group and each of $R^2$, $R^3$ and $R^4$ is a siloxyl group.

7. The organic silicon compounds of claim 2, wherein $R^1$, $R^2$, $R^3$ and $R^4$ are each independently alkyl, cycloalkyl, phenyl, benzyl or alkenyl optionally substituted with halogen atom(s).

8. The organic silicon compounds of claim 2, wherein each of $R^2$, $R^3$, and $R^4$ are a siloxyl group and each of R, $R^5$, $R^6$ and $R^7$ are independently alkyl, cycloalkyl, phenyl, benzyl or alkenyl optionally substituted with halogen atom(s).

9. The organic silicon compounds of claim 2, wherein each of $R^1$, $R^2$, $R^3$ and $R^4$ is a methyl group.

10. The organic silicon compounds of claim 2, wherein each of $R^1$, $R^5$, $R^6$ and $R^7$ is a methyl group and each of $R^2$, $R^3$ and $R^4$ is a siloxyl group.

* * * * *